United States Patent
Coward-Kelly et al.

(10) Patent No.: US 10,538,752 B2
(45) Date of Patent: Jan. 21, 2020

(54) ALPHA-AMYLASES AND POLYNUCLEOTIDES ENCODING SAME

(71) Applicant: NOVOZYMES A/S, Bagsvaerd (DK)

(72) Inventors: Guillermo Coward-Kelly, Wake Forest, NC (US); Shiro Fukuyama, Chiba (JP); Noriko Tsutsumi, Ichikawa (JP); Keiichi Ayabe, Chiba (JP)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 15/679,805

(22) Filed: Aug. 17, 2017

(65) Prior Publication Data

US 2017/0349887 A1   Dec. 7, 2017

Related U.S. Application Data

(62) Division of application No. 14/653,154, filed as application No. PCT/US2013/074957 on Dec. 13, 2013, now Pat. No. 9,765,317.

(60) Provisional application No. 61/738,145, filed on Dec. 17, 2012.

(51) Int. Cl.
| | | |
|---|---|---|
| C12N 9/26 | (2006.01) | |
| C12N 1/14 | (2006.01) | |
| C12N 1/16 | (2006.01) | |
| C12N 1/20 | (2006.01) | |
| C12N 9/30 | (2006.01) | |
| C12G 3/02 | (2019.01) | |
| C12P 19/14 | (2006.01) | |
| C12P 21/02 | (2006.01) | |
| C12P 7/06 | (2006.01) | |
| C12C 7/04 | (2006.01) | |
| C12C 5/00 | (2006.01) | |

(52) U.S. Cl.
CPC .............. *C12N 9/242* (2013.01); *C12C 5/004* (2013.01); *C12C 7/04* (2013.01); *C12G 3/02* (2013.01); *C12N 1/14* (2013.01); *C12N 1/16* (2013.01); *C12N 1/20* (2013.01); *C12N 9/2414* (2013.01); *C12P 7/06* (2013.01); *C12P 19/14* (2013.01); *C12P 21/02* (2013.01); *C12Y 302/01001* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 7,883,883 B2 | 2/2011 | Udagawa | |
| 8,945,889 B2 | 2/2015 | Ge | |
| 9,765,317 B2 * | 9/2017 | Kelly | ............... C12N 9/242 |
| 2011/0039308 A1 | 2/2011 | Slupska | |
| 2011/0097779 A1 | 4/2011 | Soong | |
| 2015/0337277 A1 | 11/2015 | Kelly | |
| 2015/0376668 A1 | 12/2015 | Ge | |
| 2016/0010128 A1 | 1/2016 | Ge | |

FOREIGN PATENT DOCUMENTS

| | | |
|---|---|---|
| WO | 2008/080093 A2 | 7/2008 |
| WO | 2010/091221 A1 | 8/2010 |
| WO | 2011/127802 A1 | 10/2011 |

OTHER PUBLICATIONS

Birren et al, 2006—Uniport Access No. Q0C881.
Birren et al, 2008, Genbank Access No. XP_001209405.1.
Matsuura et al, 1984, J Biochem 95, 697-702.

\* cited by examiner

*Primary Examiner* — Richard C Ekstrom
(74) *Attorney, Agent, or Firm* — David Fazzolare

(57) ABSTRACT

The present disclosure relates to isolated polypeptides having alpha-amylase activity, polynucleotides encoding the polypeptides, nucleic acid constructs, vectors, and host cells comprising the polynucleotides as well as methods of producing the polypeptides, and method of using polypeptides, including in ethanol production processes.

20 Claims, No Drawings
Specification includes a Sequence Listing.

SEQUENCE LISTING

```
<160> NUMBER OF SEQ ID NOS: 6

<210> SEQ ID NO 1
<211> LENGTH: 1821
<212> TYPE: DNA
<213> ORGANISM: Artificial Sequence
<220> FEATURE:
<223> OTHER INFORMATION: hybrid
<220> FEATURE:
<221> NAME/KEY: sig_peptide
<222> LOCATION: (1)..(63)
<220> FEATURE:
<221> NAME/KEY: CDS
<222> LOCATION: (1)..(1818)
<220> FEATURE:
<221> NAME/KEY: mat_peptide
<222> LOCATION: (64)..(1818)

<400> SEQUENCE: 1 atg aga tta tcg act tcg agt ctc ttc ctt tcc gtg tct ctg ctg ggg      48
Met Arg Leu Ser Thr Ser Ser Leu Phe Leu Ser Val Ser Leu Leu Gly
    -20              -15                 -10 aag ctg gcc ctc ggg ctg acc cca gca gaa tgg cgc agc cag tca atc      96
Lys Leu Ala Leu Gly Leu Thr Pro Ala Glu Trp Arg Ser Gln Ser Ile
 -5              -1   1               5                  10 tac ttc ctg ttg acc gat cgc ttt ggt cga acg gac aat tcc aca act     144
Tyr Phe Leu Leu Thr Asp Arg Phe Gly Arg Thr Asp Asn Ser Thr Thr
                15                  20                  25 gcc gct tgc gat acc tct gac aga gta tac tgc ggt ggt agc tgg cag     192
Ala Ala Cys Asp Thr Ser Asp Arg Val Tyr Cys Gly Gly Ser Trp Gln
            30                  35                  40 gga atc atc aac caa ctc gat tac atc caa ggg atg gga ttc act gcc     240
Gly Ile Ile Asn Gln Leu Asp Tyr Ile Gln Gly Met Gly Phe Thr Ala
        45                  50                  55 atc tgg atc acc ccg gtc act gga cag ttc tac gaa aac acg ggc gac     288
Ile Trp Ile Thr Pro Val Thr Gly Gln Phe Tyr Glu Asn Thr Gly Asp
 60                  65                  70                  75 ggc acc tct tac cat gga tac tgg cag cag gac atc tac gat ctc aac     336
Gly Thr Ser Tyr His Gly Tyr Trp Gln Gln Asp Ile Tyr Asp Leu Asn
                 80                  85                  90
```

```
tac aac tac gga acg gcc caa gac ctc aag aac cta gcc aat gct ttg      384
Tyr Asn Tyr Gly Thr Ala Gln Asp Leu Lys Asn Leu Ala Asn Ala Leu
             95                 100                 105 cac gag cgc ggc atg tat ttg atg gtt gat gtg gtt gcc aac cac atg      432
His Glu Arg Gly Met Tyr Leu Met Val Asp Val Val Ala Asn His Met
        110                 115                 120 ggc tat gac gga gcg gga aac acc gtg gac tac agt gtt ttc aac ccc      480
Gly Tyr Asp Gly Ala Gly Asn Thr Val Asp Tyr Ser Val Phe Asn Pro
    125                 130                 135 ttc tcc tcc tcc tcc tac ttt cac cca tac tgc ctc atc tcc aat tac      528
Phe Ser Ser Ser Ser Tyr Phe His Pro Tyr Cys Leu Ile Ser Asn Tyr
140                 145                 150                 155 gac aac cag acc aat gtt gaa gac tgc tgg ctg ggc gat acc acc gtt      576
Asp Asn Gln Thr Asn Val Glu Asp Cys Trp Leu Gly Asp Thr Thr Val
            160                 165                 170 tcg ctg cca gat ctc gac acg aca agc aca gcc gtg cgg aac atc tgg      624
Ser Leu Pro Asp Leu Asp Thr Thr Ser Thr Ala Val Arg Asn Ile Trp
        175                 180                 185 tac gac tgg gtg gca gat ttg gtc gcc aac tat tct atc gac ggt ctg      672
Tyr Asp Trp Val Ala Asp Leu Val Ala Asn Tyr Ser Ile Asp Gly Leu
    190                 195                 200 cgt gtc gac act gta aaa cac gtc gaa aaa gac ttt tgg ccc ggc tat      720
Arg Val Asp Thr Val Lys His Val Glu Lys Asp Phe Trp Pro Gly Tyr
205                 210                 215 aac agc gca gca ggc gtc tac tgt gtc ggc gag gtc tac tca ggc gat      768
Asn Ser Ala Ala Gly Val Tyr Cys Val Gly Glu Val Tyr Ser Gly Asp
220                 225                 230                 235 cct gca tac aca tgc ccg tac cag aac tac atg gac ggt gtg ctc aac      816
Pro Ala Tyr Thr Cys Pro Tyr Gln Asn Tyr Met Asp Gly Val Leu Asn
        240                 245                 250 tat cca att tac tac cag ctt ctc tat gcg ttt gag tcg tcc agc ggc      864
Tyr Pro Ile Tyr Tyr Gln Leu Leu Tyr Ala Phe Glu Ser Ser Ser Gly
            255                 260                 265 agc atc agc gat ctc tac aac atg atc agc tcc gtt gcc tcc agc tgc      912
Ser Ile Ser Asp Leu Tyr Asn Met Ile Ser Ser Val Ala Ser Ser Cys
        270                 275                 280 aag gat ccc aca ctc ctg ggg aac ttc atc gag aac cac gat aac ccc      960
Lys Asp Pro Thr Leu Leu Gly Asn Phe Ile Glu Asn His Asp Asn Pro
285                 290                 295 cgc ttc gct tcc tac acg agc gac tac tcg cag gct aag aac gtg atc     1008
Arg Phe Ala Ser Tyr Thr Ser Asp Tyr Ser Gln Ala Lys Asn Val Ile
300                 305                 310                 315 acc ttc atc ttc ctg agc gac ggt atc ccc atc gtc tac gcc gga cag     1056
Thr Phe Ile Phe Leu Ser Asp Gly Ile Pro Ile Val Tyr Ala Gly Gln
        320                 325                 330 gaa cag cac tac agc gga ggc agc gac cca gct aac cgc gag gcc acc     1104
Glu Gln His Tyr Ser Gly Gly Ser Asp Pro Ala Asn Arg Glu Ala Thr
            335                 340                 345 tgg ctg tcc gga tac tcc acc agc gct acg ctg tac acc tgg atc gcc     1152
Trp Leu Ser Gly Tyr Ser Thr Ser Ala Thr Leu Tyr Thr Trp Ile Ala
        350                 355                 360 acc aca aac cag atc cgc agc ctg gcg atc tcc aag gac gcg gga tac     1200
Thr Thr Asn Gln Ile Arg Ser Leu Ala Ile Ser Lys Asp Ala Gly Tyr
365                 370                 375 gtg cag gcc aag aac aac ccc ttc tac tcc gac tcc aac acc atc gcc     1248
Val Gln Ala Lys Asn Asn Pro Phe Tyr Ser Asp Ser Asn Thr Ile Ala
380                 385                 390                 395 atg cgc aag ggc acg aca gcc ggc gcg caa gtc atc acc gtc ctc agc     1296
Met Arg Lys Gly Thr Thr Ala Gly Ala Gln Val Ile Thr Val Leu Ser
        400                 405                 410
```

```
aac aag ggc gcc tcc ggc agc tcc tac act ctc tct ttg agt ggt acc      1344
Asn Lys Gly Ala Ser Gly Ser Ser Tyr Thr Leu Ser Leu Ser Gly Thr
            415                 420                 425 ggc tac tcc gcc ggc gtg acc ctg gtc gag acg tac acc tgc acc acg      1392
Gly Tyr Ser Ala Gly Val Thr Leu Val Glu Thr Tyr Thr Cys Thr Thr
                430                 435                 440 gtg act gta gac tcg agc ggc aac ctg ccc gtc cca atg aca tcc ggc      1440
Val Thr Val Asp Ser Ser Gly Asn Leu Pro Val Pro Met Thr Ser Gly
    445                 450                 455 ttg ccg cga gtg ttt gtc ccg tcg tcc tgg gtg aat ggg agc gcg ctt      1488
Leu Pro Arg Val Phe Val Pro Ser Ser Trp Val Asn Gly Ser Ala Leu
460                 465                 470                 475 tgc aac ggt gct aca agc ccg ggt ggc tcc tcg ggt agt gtc gag gtc      1536
Cys Asn Gly Ala Thr Ser Pro Gly Gly Ser Ser Gly Ser Val Glu Val
                480                 485                 490 act ttc gac gtt tac gct acc aca gta tat ggc cag aac atc tat atc      1584
Thr Phe Asp Val Tyr Ala Thr Thr Val Tyr Gly Gln Asn Ile Tyr Ile
                495                 500                 505 acc ggt gat gtg agt gag ctc ggc aac tgg aca ccc gcc aat ggt gtt      1632
Thr Gly Asp Val Ser Glu Leu Gly Asn Trp Thr Pro Ala Asn Gly Val
    510                 515                 520 gca ctc tct tct gct aac tac ccc acc tgg agt gcc acg atc gct ctc      1680
Ala Leu Ser Ser Ala Asn Tyr Pro Thr Trp Ser Ala Thr Ile Ala Leu
525                 530                 535 ccc gct gac acg aca atc cag tac aag tat gtc aac att gac ggc agc      1728
Pro Ala Asp Thr Thr Ile Gln Tyr Lys Tyr Val Asn Ile Asp Gly Ser
540                 545                 550                 555 acc gtc atc tgg gag gat gct atc agc aat cgc gag atc acg acg ccc      1776
Thr Val Ile Trp Glu Asp Ala Ile Ser Asn Arg Glu Ile Thr Thr Pro
                560                 565                 570 gcc agc ggc aca tac acc gaa aaa gac act tgg gat gaa tct tag          1821
Ala Ser Gly Thr Tyr Thr Glu Lys Asp Thr Trp Asp Glu Ser
                575                 580                 585

<210> SEQ ID NO 2
<211> LENGTH: 606
<212> TYPE: PRT
<213> ORGANISM: Artificial Sequence
<220> FEATURE:
<223> OTHER INFORMATION: Synthetic Construct

<400> SEQUENCE: 2

Met Arg Leu Ser Thr Ser Ser Leu Phe Leu Ser Val Ser Leu Leu Gly
        -20                 -15                 -10

Lys Leu Ala Leu Gly Leu Thr Pro Ala Glu Trp Arg Ser Gln Ser Ile
 -5              -1   1               5                  10

Tyr Phe Leu Leu Thr Asp Arg Phe Gly Arg Thr Asp Asn Ser Thr Thr
                15                  20                  25

Ala Ala Cys Asp Thr Ser Asp Arg Val Tyr Cys Gly Gly Ser Trp Gln
            30                  35                  40

Gly Ile Ile Asn Gln Leu Asp Tyr Ile Gln Gly Met Gly Phe Thr Ala
    45                  50                  55

Ile Trp Ile Thr Pro Val Thr Gly Gln Phe Tyr Glu Asn Thr Gly Asp
60                  65                  70                  75

Gly Thr Ser Tyr His Gly Tyr Trp Gln Gln Asp Ile Tyr Asp Leu Asn
                80                  85                  90

Tyr Asn Tyr Gly Thr Ala Gln Asp Leu Lys Asn Leu Ala Asn Ala Leu
            95                  100                 105
```

```
His Glu Arg Gly Met Tyr Leu Met Val Asp Val Ala Asn His Met
            110                 115                 120
Gly Tyr Asp Gly Ala Gly Asn Thr Val Asp Tyr Ser Val Phe Asn Pro
125                 130                 135
Phe Ser Ser Ser Tyr Phe His Pro Tyr Cys Leu Ile Ser Asn Tyr
140                 145                 150                 155
Asp Asn Gln Thr Asn Val Glu Asp Cys Trp Leu Gly Asp Thr Thr Val
                160                 165                 170
Ser Leu Pro Asp Leu Asp Thr Thr Ser Thr Ala Val Arg Asn Ile Trp
            175                 180                 185
Tyr Asp Trp Val Ala Asp Leu Val Ala Asn Tyr Ser Ile Asp Gly Leu
            190                 195                 200
Arg Val Asp Thr Val Lys His Val Glu Lys Asp Phe Trp Pro Gly Tyr
205                 210                 215
Asn Ser Ala Ala Gly Val Tyr Cys Val Gly Glu Val Tyr Ser Gly Asp
220                 225                 230                 235
Pro Ala Tyr Thr Cys Pro Tyr Gln Asn Tyr Met Asp Gly Val Leu Asn
                240                 245                 250
Tyr Pro Ile Tyr Tyr Gln Leu Leu Tyr Ala Phe Glu Ser Ser Ser Gly
            255                 260                 265
Ser Ile Ser Asp Leu Tyr Asn Met Ile Ser Ser Val Ala Ser Ser Cys
            270                 275                 280
Lys Asp Pro Thr Leu Leu Gly Asn Phe Ile Glu Asn His Asp Asn Pro
285                 290                 295
Arg Phe Ala Ser Tyr Thr Ser Asp Tyr Ser Gln Ala Lys Asn Val Ile
300                 305                 310                 315
Thr Phe Ile Phe Leu Ser Asp Gly Ile Pro Ile Val Tyr Ala Gly Gln
                320                 325                 330
Glu Gln His Tyr Ser Gly Gly Ser Asp Pro Ala Asn Arg Glu Ala Thr
            335                 340                 345
Trp Leu Ser Gly Tyr Ser Thr Ser Ala Thr Leu Tyr Thr Trp Ile Ala
            350                 355                 360
Thr Thr Asn Gln Ile Arg Ser Leu Ala Ile Ser Lys Asp Ala Gly Tyr
            365                 370                 375
Val Gln Ala Lys Asn Asn Pro Phe Tyr Ser Asp Ser Asn Thr Ile Ala
380                 385                 390                 395
Met Arg Lys Gly Thr Thr Ala Gly Ala Gln Val Ile Thr Val Leu Ser
                400                 405                 410
Asn Lys Gly Ala Ser Gly Ser Ser Tyr Thr Leu Ser Leu Ser Gly Thr
            415                 420                 425
Gly Tyr Ser Ala Gly Val Thr Leu Val Glu Thr Tyr Thr Cys Thr Thr
            430                 435                 440
Val Thr Val Asp Ser Ser Gly Asn Leu Pro Val Pro Met Thr Ser Gly
            445                 450                 455
Leu Pro Arg Val Phe Val Pro Ser Ser Trp Val Asn Gly Ser Ala Leu
460                 465                 470                 475
Cys Asn Gly Ala Thr Ser Pro Gly Gly Ser Ser Gly Ser Val Glu Val
                480                 485                 490
Thr Phe Asp Val Tyr Ala Thr Thr Val Tyr Gly Gln Asn Ile Tyr Ile
            495                 500                 505
Thr Gly Asp Val Ser Glu Leu Gly Asn Trp Thr Pro Ala Asn Gly Val
            510                 515                 520
```

```
Ala Leu Ser Ser Ala Asn Tyr Pro Thr Trp Ser Ala Thr Ile Ala Leu
        525                 530                 535

Pro Ala Asp Thr Thr Ile Gln Tyr Lys Tyr Val Asn Ile Asp Gly Ser
540                 545                 550                 555

Thr Val Ile Trp Glu Asp Ala Ile Ser Asn Arg Glu Ile Thr Thr Pro
                560                 565                 570

Ala Ser Gly Thr Tyr Thr Glu Lys Asp Thr Trp Asp Glu Ser
                575                 580                 585

<210> SEQ ID NO 3
<211> LENGTH: 1932
<212> TYPE: DNA
<213> ORGANISM: Artificial Sequence
<220> FEATURE:
<223> OTHER INFORMATION: Hybrid
<220> FEATURE:
<221> NAME/KEY: sig_peptide
<222> LOCATION: (1)..(63)
<220> FEATURE:
<221> NAME/KEY: CDS
<222> LOCATION: (1)..(1929)
<220> FEATURE:
<221> NAME/KEY: mat_peptide
<222> LOCATION: (64)..(1929)

<400> SEQUENCE: 3
```

| | | | | | | | | | | | | | | | | |
|---|---|---|---|---|---|---|---|---|---|---|---|---|---|---|---|---|
| atg aga tta tcg act tcg agt ctc ttc ctt tcc gtg tct ctg ctg ggg | | | | | | | | | | | | | | | | 48 |
| Met Arg Leu Ser Thr Ser Ser Leu Phe Leu Ser Val Ser Leu Leu Gly | | | | | | | | | | | | | | | | |
| -20 | | | | -15 | | | | | -10 | | | | | | | |
| aag ctg gcc ctc ggg ctg acc cca gca gaa tgg cgc agc cag tca atc | | | | | | | | | | | | | | | | 96 |
| Lys Leu Ala Leu Gly Leu Thr Pro Ala Glu Trp Arg Ser Gln Ser Ile | | | | | | | | | | | | | | | | |
| -5 | | | | -1 1 | | | | 5 | | | | | | 10 | | |
| tac ttc ctg ttg acc gat cgc ttt ggt cga acg gac aat tcc aca act | | | | | | | | | | | | | | | | 144 |
| Tyr Phe Leu Leu Thr Asp Arg Phe Gly Arg Thr Asp Asn Ser Thr Thr | | | | | | | | | | | | | | | | |
| | | | 15 | | | | | 20 | | | | | 25 | | | |
| gcc gct tgc gat acc tct gac aga gta tac tgc ggt ggt agc tgg cag | | | | | | | | | | | | | | | | 192 |
| Ala Ala Cys Asp Thr Ser Asp Arg Val Tyr Cys Gly Gly Ser Trp Gln | | | | | | | | | | | | | | | | |
| | | 30 | | | | | 35 | | | | | 40 | | | | |
| gga atc atc aac caa ctc gat tac atc caa ggg atg gga ttc act gcc | | | | | | | | | | | | | | | | 240 |
| Gly Ile Ile Asn Gln Leu Asp Tyr Ile Gln Gly Met Gly Phe Thr Ala | | | | | | | | | | | | | | | | |
| | 45 | | | | | 50 | | | | | 55 | | | | | |
| atc tgg atc acc ccg gtc act gga cag ttc tac gaa aac acg ggc gac | | | | | | | | | | | | | | | | 288 |
| Ile Trp Ile Thr Pro Val Thr Gly Gln Phe Tyr Glu Asn Thr Gly Asp | | | | | | | | | | | | | | | | |
| 60 | | | | | 65 | | | | | 70 | | | | | 75 | |
| ggc acc tct tac cat gga tac tgg cag cag gac atc tac gat ctc aac | | | | | | | | | | | | | | | | 336 |
| Gly Thr Ser Tyr His Gly Tyr Trp Gln Gln Asp Ile Tyr Asp Leu Asn | | | | | | | | | | | | | | | | |
| | | | | 80 | | | | | 85 | | | | | 90 | | |
| tac aac tac gga acg gcc caa gac ctc aag aac cta gcc aat gct ttg | | | | | | | | | | | | | | | | 384 |
| Tyr Asn Tyr Gly Thr Ala Gln Asp Leu Lys Asn Leu Ala Asn Ala Leu | | | | | | | | | | | | | | | | |
| | | | 95 | | | | | 100 | | | | | 105 | | | |
| cac gag cgc ggc atg tat ttg atg gtt gat gtg gtt gcc aac cac atg | | | | | | | | | | | | | | | | 432 |
| His Glu Arg Gly Met Tyr Leu Met Val Asp Val Val Ala Asn His Met | | | | | | | | | | | | | | | | |
| | | 110 | | | | | 115 | | | | | 120 | | | | |
| ggc tat gac gga gcg gga aac acc gtg gac tac agt gtt ttc aac ccc | | | | | | | | | | | | | | | | 480 |
| Gly Tyr Asp Gly Ala Gly Asn Thr Val Asp Tyr Ser Val Phe Asn Pro | | | | | | | | | | | | | | | | |
| | 125 | | | | | 130 | | | | | 135 | | | | | |
| ttc tcc tcc tcc tcc tac ttt cac cca tac tgc ctc atc tcc aat tac | | | | | | | | | | | | | | | | 528 |
| Phe Ser Ser Ser Ser Tyr Phe His Pro Tyr Cys Leu Ile Ser Asn Tyr | | | | | | | | | | | | | | | | |
| 140 | | | | | 145 | | | | | 150 | | | | | 155 | |
| gac aac cag acc aat gtt gaa gac tgc tgg ctg ggc gat acc acc gtt | | | | | | | | | | | | | | | | 576 |
| Asp Asn Gln Thr Asn Val Glu Asp Cys Trp Leu Gly Asp Thr Thr Val | | | | | | | | | | | | | | | | |
| | | | | 160 | | | | | 165 | | | | | 170 | | |

-continued

| | | | | | | | | | | | | | | | | |
|---|---|---|---|---|---|---|---|---|---|---|---|---|---|---|---|---|
| tcg | ctg | cca | gat | ctc | gac | acg | aca | agc | aca | gcc | gtg | cgg | aac | atc | tgg | 624 |
| Ser | Leu | Pro | Asp | Leu | Asp | Thr | Thr | Ser | Thr | Ala | Val | Arg | Asn | Ile | Trp | |
| | | 175 | | | | | 180 | | | | | 185 | | | | |
| tac | gac | tgg | gtg | gca | gat | ttg | gtc | gcc | aac | tat | tct | atc | gac | ggt | ctg | 672 |
| Tyr | Asp | Trp | Val | Ala | Asp | Leu | Val | Ala | Asn | Tyr | Ser | Ile | Asp | Gly | Leu | |
| | | 190 | | | | | 195 | | | | | 200 | | | | |
| cgt | gtc | gac | act | gta | aaa | cac | gtc | gaa | aaa | gac | ttt | tgg | ccc | ggc | tat | 720 |
| Arg | Val | Asp | Thr | Val | Lys | His | Val | Glu | Lys | Asp | Phe | Trp | Pro | Gly | Tyr | |
| | 205 | | | | | 210 | | | | | 215 | | | | | |
| aac | agc | gca | gca | ggc | gtc | tac | tgt | gtc | ggc | gag | gtc | tac | tca | ggc | gat | 768 |
| Asn | Ser | Ala | Ala | Gly | Val | Tyr | Cys | Val | Gly | Glu | Val | Tyr | Ser | Gly | Asp | |
| 220 | | | | | 225 | | | | | 230 | | | | | 235 | |
| cct | gca | tac | aca | tgc | ccg | tac | cag | aac | tac | atg | gac | ggt | gtg | ctc | aac | 816 |
| Pro | Ala | Tyr | Thr | Cys | Pro | Tyr | Gln | Asn | Tyr | Met | Asp | Gly | Val | Leu | Asn | |
| | | | 240 | | | | | 245 | | | | | 250 | | | |
| tat | cca | att | tac | tac | cag | ctt | ctc | tat | gcg | ttt | gag | tcg | tcc | agc | ggc | 864 |
| Tyr | Pro | Ile | Tyr | Tyr | Gln | Leu | Leu | Tyr | Ala | Phe | Glu | Ser | Ser | Ser | Gly | |
| | | | 255 | | | | | 260 | | | | | 265 | | | |
| agc | atc | agc | gat | ctc | tac | aac | atg | atc | agc | tcc | gtt | gcc | tcc | agc | tgc | 912 |
| Ser | Ile | Ser | Asp | Leu | Tyr | Asn | Met | Ile | Ser | Ser | Val | Ala | Ser | Ser | Cys | |
| | | 270 | | | | | 275 | | | | | 280 | | | | |
| aag | gat | ccc | aca | ctc | ctg | ggg | aac | ttc | atc | gag | aac | cac | gat | aac | ccc | 960 |
| Lys | Asp | Pro | Thr | Leu | Leu | Gly | Asn | Phe | Ile | Glu | Asn | His | Asp | Asn | Pro | |
| 285 | | | | | 290 | | | | | 295 | | | | | | |
| cgc | ttc | gct | tcc | tac | acg | agc | gac | tac | tcg | cag | gct | aag | aac | gtg | atc | 1008 |
| Arg | Phe | Ala | Ser | Tyr | Thr | Ser | Asp | Tyr | Ser | Gln | Ala | Lys | Asn | Val | Ile | |
| 300 | | | | | 305 | | | | | 310 | | | | | 315 | |
| acc | ttc | atc | ttc | ctg | agc | gac | ggt | atc | ccc | atc | gtc | tac | gcc | gga | cag | 1056 |
| Thr | Phe | Ile | Phe | Leu | Ser | Asp | Gly | Ile | Pro | Ile | Val | Tyr | Ala | Gly | Gln | |
| | | | 320 | | | | | 325 | | | | | 330 | | | |
| gaa | cag | cac | tac | agc | gga | ggc | agc | gac | cca | gct | aac | cgc | gag | gcc | acc | 1104 |
| Glu | Gln | His | Tyr | Ser | Gly | Gly | Ser | Asp | Pro | Ala | Asn | Arg | Glu | Ala | Thr | |
| | | | 335 | | | | | 340 | | | | | 345 | | | |
| tgg | ctg | tcc | gga | tac | tcc | acc | agc | gct | acg | ctg | tac | acc | tgg | atc | gcc | 1152 |
| Trp | Leu | Ser | Gly | Tyr | Ser | Thr | Ser | Ala | Thr | Leu | Tyr | Thr | Trp | Ile | Ala | |
| | | 350 | | | | | 355 | | | | | 360 | | | | |
| acc | aca | aac | cag | atc | cgc | agc | ctg | gcg | atc | tcc | aag | gac | gcg | gga | tac | 1200 |
| Thr | Thr | Asn | Gln | Ile | Arg | Ser | Leu | Ala | Ile | Ser | Lys | Asp | Ala | Gly | Tyr | |
| 365 | | | | | 370 | | | | | 375 | | | | | | |
| gtg | cag | gcc | aag | aac | aac | ccc | ttc | tac | tcc | gac | tcc | aac | acc | atc | gcc | 1248 |
| Val | Gln | Ala | Lys | Asn | Asn | Pro | Phe | Tyr | Ser | Asp | Ser | Asn | Thr | Ile | Ala | |
| 380 | | | | | 385 | | | | | 390 | | | | | 395 | |
| atg | cgc | aag | ggc | acg | aca | gcc | ggc | gcg | caa | gtc | atc | acc | gtc | ctc | agc | 1296 |
| Met | Arg | Lys | Gly | Thr | Thr | Ala | Gly | Ala | Gln | Val | Ile | Thr | Val | Leu | Ser | |
| | | | 400 | | | | | 405 | | | | | 410 | | | |
| aac | aag | ggc | gcc | tcc | ggc | agc | tcc | tac | act | ctc | tct | ttg | agt | ggt | acc | 1344 |
| Asn | Lys | Gly | Ala | Ser | Gly | Ser | Ser | Tyr | Thr | Leu | Ser | Leu | Ser | Gly | Thr | |
| | | | 415 | | | | | 420 | | | | | 425 | | | |
| ggc | tac | tcc | gcc | ggc | gtg | acc | ctg | gtc | gag | acg | tac | acc | tgc | acc | acg | 1392 |
| Gly | Tyr | Ser | Ala | Gly | Val | Thr | Leu | Val | Glu | Thr | Tyr | Thr | Cys | Thr | Thr | |
| | | 430 | | | | | 435 | | | | | 440 | | | | |
| gtg | act | gta | gac | tcg | agc | ggc | aac | ctg | ccc | gtc | cca | atg | aca | tcc | ggc | 1440 |
| Val | Thr | Val | Asp | Ser | Ser | Gly | Asn | Leu | Pro | Val | Pro | Met | Thr | Ser | Gly | |
| | | 445 | | | | | 450 | | | | | 455 | | | | |
| ttg | ccg | cga | gtg | ttt | gtc | ccg | tcg | tcc | tgg | gtg | aat | ggg | agc | gcg | ctt | 1488 |
| Leu | Pro | Arg | Val | Phe | Val | Pro | Ser | Ser | Trp | Val | Asn | Gly | Ser | Ala | Leu | |
| 460 | | | | 465 | | | | | 470 | | | | | 475 | | |
| tgc | aac | act | ggc | ggc | acc | act | acg | gct | acc | ccc | act | ggc | tcc | ggc | | 1536 |
| Cys | Asn | Thr | Gly | Gly | Thr | Thr | Thr | Ala | Thr | Pro | Thr | Gly | Ser | Gly | | |
| | | | 480 | | | | | 485 | | | | | 490 | | | |

```
agc gtg acc tcg acc agc aag acc acc gcg act gcc agc aag acc agc    1584
Ser Val Thr Ser Thr Ser Lys Thr Thr Ala Thr Ala Ser Lys Thr Ser
        495                 500                 505 acc agt acg tca tca acc tcc tgt acc act ccc acc gcc gtg gct gtg    1632
Thr Ser Thr Ser Ser Thr Ser Cys Thr Thr Pro Thr Ala Val Ala Val
        510                 515                 520 act ttc gat ctg aca gct acc acc acc tac ggc gag aac atc tac ctg    1680
Thr Phe Asp Leu Thr Ala Thr Thr Thr Tyr Gly Glu Asn Ile Tyr Leu
        525                 530                 535 gtc gga tcg atc tct cag ctg ggt gac tgg gaa acc agc gac ggc ata    1728
Val Gly Ser Ile Ser Gln Leu Gly Asp Trp Glu Thr Ser Asp Gly Ile
540                 545                 550                 555 gct ctg agt gct gac aag tac act tcc agc gac ccg ctc tgg tat gtc    1776
Ala Leu Ser Ala Asp Lys Tyr Thr Ser Ser Asp Pro Leu Trp Tyr Val
                560                 565                 570 act gtg act ctg ccg gct ggt gag tcg ttt gag tac aag ttt atc cgc    1824
Thr Val Thr Leu Pro Ala Gly Glu Ser Phe Glu Tyr Lys Phe Ile Arg
        575                 580                 585 att gag agc gat gac tcc gtg gag tgg gag agt gat ccc aac cga gaa    1872
Ile Glu Ser Asp Asp Ser Val Glu Trp Glu Ser Asp Pro Asn Arg Glu
        590                 595                 600 tac acc gtt cct cag gcg tgc gga acg tcg acc gcg acg gtg act gac    1920
Tyr Thr Val Pro Gln Ala Cys Gly Thr Ser Thr Ala Thr Val Thr Asp
    605                 610                 615 acc tgg cgg tag                                                    1932
Thr Trp Arg
620

<210> SEQ ID NO 4
<211> LENGTH: 643
<212> TYPE: PRT
<213> ORGANISM: Artificial Sequence
<220> FEATURE:
<223> OTHER INFORMATION: Synthetic Construct

<400> SEQUENCE: 4

Met Arg Leu Ser Thr Ser Ser Leu Phe Leu Ser Val Ser Leu Leu Gly
        -20                 -15                 -10

Lys Leu Ala Leu Gly Leu Thr Pro Ala Glu Trp Arg Ser Gln Ser Ile
-5              -1  1               5                   10

Tyr Phe Leu Leu Thr Asp Arg Phe Gly Arg Thr Asp Asn Ser Thr Thr
            15                  20                  25

Ala Ala Cys Asp Thr Ser Asp Arg Val Tyr Cys Gly Gly Ser Trp Gln
        30                  35                  40

Gly Ile Ile Asn Gln Leu Asp Tyr Ile Gln Gly Met Gly Phe Thr Ala
    45                  50                  55

Ile Trp Ile Thr Pro Val Thr Gly Gln Phe Tyr Glu Asn Thr Gly Asp
60                  65                  70                  75

Gly Thr Ser Tyr His Gly Tyr Trp Gln Gln Asp Ile Tyr Asp Leu Asn
                80                  85                  90

Tyr Asn Tyr Gly Thr Ala Gln Asp Leu Lys Asn Leu Ala Asn Ala Leu
            95                  100                 105

His Glu Arg Gly Met Tyr Leu Met Val Asp Val Val Ala Asn His Met
        110                 115                 120

Gly Tyr Asp Gly Ala Gly Asn Thr Val Asp Tyr Ser Val Phe Asn Pro
    125                 130                 135

Phe Ser Ser Ser Ser Tyr Phe His Pro Tyr Cys Leu Ile Ser Asn Tyr
140                 145                 150                 155
```

-continued

```
Asp Asn Gln Thr Asn Val Glu Asp Cys Trp Leu Gly Asp Thr Thr Val
            160                 165                 170
Ser Leu Pro Asp Leu Asp Thr Thr Ser Thr Ala Val Arg Asn Ile Trp
        175                 180                 185
Tyr Asp Trp Val Ala Asp Leu Val Ala Asn Tyr Ser Ile Asp Gly Leu
            190                 195                 200
Arg Val Asp Thr Val Lys His Val Glu Lys Asp Phe Trp Pro Gly Tyr
        205                 210                 215
Asn Ser Ala Ala Gly Val Tyr Cys Val Gly Glu Val Tyr Ser Gly Asp
220                 225                 230                 235
Pro Ala Tyr Thr Cys Pro Tyr Gln Asn Tyr Met Asp Gly Val Leu Asn
            240                 245                 250
Tyr Pro Ile Tyr Tyr Gln Leu Leu Tyr Ala Phe Glu Ser Ser Ser Gly
        255                 260                 265
Ser Ile Ser Asp Leu Tyr Asn Met Ile Ser Ser Val Ala Ser Ser Cys
        270                 275                 280
Lys Asp Pro Thr Leu Leu Gly Asn Phe Ile Glu Asn His Asp Asn Pro
        285                 290                 295
Arg Phe Ala Ser Tyr Thr Ser Asp Tyr Ser Gln Ala Lys Asn Val Ile
300                 305                 310                 315
Thr Phe Ile Phe Leu Ser Asp Gly Ile Pro Ile Val Tyr Ala Gly Gln
            320                 325                 330
Glu Gln His Tyr Ser Gly Gly Ser Asp Pro Ala Asn Arg Glu Ala Thr
        335                 340                 345
Trp Leu Ser Gly Tyr Ser Thr Ser Ala Thr Leu Tyr Thr Trp Ile Ala
        350                 355                 360
Thr Thr Asn Gln Ile Arg Ser Leu Ala Ile Ser Lys Asp Ala Gly Tyr
        365                 370                 375
Val Gln Ala Lys Asn Asn Pro Phe Tyr Ser Asp Ser Asn Thr Ile Ala
380                 385                 390                 395
Met Arg Lys Gly Thr Thr Ala Gly Ala Gln Val Ile Thr Val Leu Ser
            400                 405                 410
Asn Lys Gly Ala Ser Gly Ser Ser Tyr Thr Leu Ser Leu Ser Gly Thr
            415                 420                 425
Gly Tyr Ser Ala Gly Val Thr Leu Val Glu Thr Tyr Thr Cys Thr Thr
        430                 435                 440
Val Thr Val Asp Ser Ser Gly Asn Leu Pro Val Pro Met Thr Ser Gly
        445                 450                 455
Leu Pro Arg Val Phe Val Pro Ser Ser Trp Val Asn Gly Ser Ala Leu
460                 465                 470                 475
Cys Asn Thr Gly Gly Thr Thr Thr Ala Thr Pro Thr Gly Ser Gly
            480                 485                 490
Ser Val Thr Ser Thr Ser Lys Thr Thr Ala Thr Ala Ser Lys Thr Ser
            495                 500                 505
Thr Ser Thr Ser Ser Thr Ser Cys Thr Thr Pro Thr Ala Val Ala Val
        510                 515                 520
Thr Phe Asp Leu Thr Ala Thr Thr Tyr Gly Glu Asn Ile Tyr Leu
        525                 530                 535
Val Gly Ser Ile Ser Gln Leu Gly Asp Trp Glu Thr Ser Asp Gly Ile
540                 545                 550                 555
Ala Leu Ser Ala Asp Lys Tyr Thr Ser Ser Asp Pro Leu Trp Tyr Val
            560                 565                 570
```

```
                                                  -continued

Thr Val Thr Leu Pro Ala Gly Glu Ser Phe Glu Tyr Lys Phe Ile Arg
            575                 580                 585

Ile Glu Ser Asp Asp Ser Val Glu Trp Glu Ser Asp Pro Asn Arg Glu
        590                 595                 600

Tyr Thr Val Pro Gln Ala Cys Gly Thr Ser Thr Ala Thr Val Thr Asp
    605                 610                 615

Thr Trp Arg
620

<210> SEQ ID NO 5
<211> LENGTH: 1887
<212> TYPE: DNA
<213> ORGANISM: Artificial Sequence
<220> FEATURE:
<223> OTHER INFORMATION: Hybrid
<220> FEATURE:
<221> NAME/KEY: sig_peptide
<222> LOCATION: (1)..(63)
<220> FEATURE:
<221> NAME/KEY: CDS
<222> LOCATION: (1)..(1884)
<220> FEATURE:
<221> NAME/KEY: mat_peptide
<222> LOCATION: (64)..(1884)

<400> SEQUENCE: 5 atg aga tta tcg act tcg agt ctc ttc ctt tcc gtg tct ctg ctg ggg      48
Met Arg Leu Ser Thr Ser Ser Leu Phe Leu Ser Val Ser Leu Leu Gly
    -20                 -15                 -10 aag ctg gcc ctc ggg ctg acc cca gca gaa tgg cgc agc cag tca atc      96
Lys Leu Ala Leu Gly Leu Thr Pro Ala Glu Trp Arg Ser Gln Ser Ile
 -5              -1   1               5                  10 tac ttc ctg ttg acc gat cgc ttt ggt cga acg gac aat tcc aca act     144
Tyr Phe Leu Leu Thr Asp Arg Phe Gly Arg Thr Asp Asn Ser Thr Thr
                 15                  20                  25 gcc gct tgc gat acc tct gac aga gta tac tgc ggt ggt agc tgg cag     192
Ala Ala Cys Asp Thr Ser Asp Arg Val Tyr Cys Gly Gly Ser Trp Gln
            30                  35                  40 gga atc atc aac caa ctc gat tac atc caa ggg atg gga ttc act gcc     240
Gly Ile Ile Asn Gln Leu Asp Tyr Ile Gln Gly Met Gly Phe Thr Ala
        45                  50                  55 atc tgg atc acc ccg gtc act gga cag ttc tac gaa aac acg ggc gac     288
Ile Trp Ile Thr Pro Val Thr Gly Gln Phe Tyr Glu Asn Thr Gly Asp
60                  65                  70                  75 ggc acc tct tac cat gga tac tgg cag cag gac atc tac gat ctc aac     336
Gly Thr Ser Tyr His Gly Tyr Trp Gln Gln Asp Ile Tyr Asp Leu Asn
                80                  85                  90 tac aac tac gga acg gcc caa gac ctc aag aac cta gcc aat gct ttg     384
Tyr Asn Tyr Gly Thr Ala Gln Asp Leu Lys Asn Leu Ala Asn Ala Leu
            95                 100                 105 cac gag cgc ggc atg tat ttg atg gtt gat gtg gtt gcc aac cac atg     432
His Glu Arg Gly Met Tyr Leu Met Val Asp Val Val Ala Asn His Met
        110                 115                 120 ggc tat gac gga gcg gga aac acc gtg gac tac agt gtt ttc aac ccc     480
Gly Tyr Asp Gly Ala Gly Asn Thr Val Asp Tyr Ser Val Phe Asn Pro
    125                 130                 135 ttc tcc tcc tcc tcc tac ttt cac cca tac tgc ctc atc tcc aat tac     528
Phe Ser Ser Ser Ser Tyr Phe His Pro Tyr Cys Leu Ile Ser Asn Tyr
140                 145                 150                 155 gac aac cag acc aat gtt gaa gac tgc tgg ctg ggc gat acc acc gtt     576
Asp Asn Gln Thr Asn Val Glu Asp Cys Trp Leu Gly Asp Thr Thr Val
                160                 165                 170
```

| | | |
|---|---|---|
| tcg ctg cca gat ctc gac acg aca agc aca gcc gtg cgg aac atc tgg<br>Ser Leu Pro Asp Leu Asp Thr Thr Ser Thr Ala Val Arg Asn Ile Trp<br>             175                        180                        185 | 624 |
| tac gac tgg gtg gca gat ttg gtc gcc aac tat tct atc gac ggt ctg<br>Tyr Asp Trp Val Ala Asp Leu Val Ala Asn Tyr Ser Ile Asp Gly Leu<br>             190                        195                        200 | 672 |
| cgt gtc gac act gta aaa cac gtc gaa aaa gac ttt tgg ccc ggc tat<br>Arg Val Asp Thr Val Lys His Val Glu Lys Asp Phe Trp Pro Gly Tyr<br>205                        210                        215 | 720 |
| aac agc gca gca ggc gtc tac tgt gtc ggc gag gtc tac tca ggc gat<br>Asn Ser Ala Ala Gly Val Tyr Cys Val Gly Glu Val Tyr Ser Gly Asp<br>220                        225                        230                        235 | 768 |
| cct gca tac aca tgc ccg tac cag aac tac atg gac ggt gtg ctc aac<br>Pro Ala Tyr Thr Cys Pro Tyr Gln Asn Tyr Met Asp Gly Val Leu Asn<br>             240                        245                        250 | 816 |
| tat cca att tac tac cag ctt ctc tat gcg ttt gag tcg tcc agc ggc<br>Tyr Pro Ile Tyr Tyr Gln Leu Leu Tyr Ala Phe Glu Ser Ser Ser Gly<br>                      255                        260                        265 | 864 |
| agc atc agc gat ctc tac aac atg atc agc tcc gtt gcc tcc agc tgc<br>Ser Ile Ser Asp Leu Tyr Asn Met Ile Ser Ser Val Ala Ser Ser Cys<br>             270                        275                        280 | 912 |
| aag gat ccc aca ctc ctg ggg aac ttc atc gag aac cac gat aac ccc<br>Lys Asp Pro Thr Leu Leu Gly Asn Phe Ile Glu Asn His Asp Asn Pro<br>285                        290                        295 | 960 |
| cgc ttc gct tcc tac acg agc gac tac tcg cag gct aag aac gtg atc<br>Arg Phe Ala Ser Tyr Thr Ser Asp Tyr Ser Gln Ala Lys Asn Val Ile<br>300                        305                        310                        315 | 1008 |
| acc ttc atc ttc ctg agc gac ggt atc ccc atc gtc tac gcc gga cag<br>Thr Phe Ile Phe Leu Ser Asp Gly Ile Pro Ile Val Tyr Ala Gly Gln<br>                      320                        325                        330 | 1056 |
| gaa cag cac tac agc gga ggc agc gac cca gct aac cgc gag gcc acc<br>Glu Gln His Tyr Ser Gly Gly Ser Asp Pro Ala Asn Arg Glu Ala Thr<br>                      335                        340                        345 | 1104 |
| tgg ctg tcc gga tac tcc acc agc gct acg ctg tac acc tgg atc gcc<br>Trp Leu Ser Gly Tyr Ser Thr Ser Ala Thr Leu Tyr Thr Trp Ile Ala<br>350                        355                        360 | 1152 |
| acc aca aac cag atc cgc agc ctg gcg atc tcc aag gac gcg gga tac<br>Thr Thr Asn Gln Ile Arg Ser Leu Ala Ile Ser Lys Asp Ala Gly Tyr<br>365                        370                        375 | 1200 |
| gtg cag gcc aag aac aac ccc ttc tac tcc gac tcc aac acc atc gcc<br>Val Gln Ala Lys Asn Asn Pro Phe Tyr Ser Asp Ser Asn Thr Ile Ala<br>380                        385                        390                        395 | 1248 |
| atg cgc aag ggc acg aca gcc ggc gcg caa gtc atc acc gtc ctc agc<br>Met Arg Lys Gly Thr Thr Ala Gly Ala Gln Val Ile Thr Val Leu Ser<br>                      400                        405                        410 | 1296 |
| aac aag ggc gcc tcc ggc agc tcc tac act ctc tct ttg agt ggt acc<br>Asn Lys Gly Ala Ser Gly Ser Ser Tyr Thr Leu Ser Leu Ser Gly Thr<br>             415                        420                        425 | 1344 |
| ggc tac tcc gcc ggc gtg acc ctg gtc gag acg tac acc tgc acc acg<br>Gly Tyr Ser Ala Gly Val Thr Leu Val Glu Thr Tyr Thr Cys Thr Thr<br>             430                        435                        440 | 1392 |
| gtg act gta gac tcg agc ggc aac ctg ccc gtc cca atg aca tcc ggc<br>Val Thr Val Asp Ser Ser Gly Asn Leu Pro Val Pro Met Thr Ser Gly<br>445                        450                        455 | 1440 |
| ttg ccg cga gtg ttt gtc ccg tcg tcc tgg gtg aat ggg agc gcg ctt<br>Leu Pro Arg Val Phe Val Pro Ser Ser Trp Val Asn Gly Ser Ala Leu<br>460                        465                        470                        475 | 1488 |
| tgc aac acg acg ggg acg ggg ggc agc act ggc act act acc gct tcc<br>Cys Asn Thr Thr Gly Thr Gly Gly Ser Thr Gly Thr Thr Thr Ala Ser<br>                      480                        485                        490 | 1536 |

```
gag acc gga gga tca tcg cca acc tcg aca gca tgc gcg tcc gtc ccc    1584
Glu Thr Gly Gly Ser Ser Pro Thr Ser Thr Ala Cys Ala Ser Val Pro
            495             500             505 gta act ttt aac gag aag gtt acg acc gtc gtc ggg gag acg atc aag    1632
Val Thr Phe Asn Glu Lys Val Thr Thr Val Val Gly Glu Thr Ile Lys
            510             515             520 ata tcc ggc agc gtg gcc gcc ctc ggc gac tgg gcc acg ggc agc gcg    1680
Ile Ser Gly Ser Val Ala Ala Leu Gly Asp Trp Ala Thr Gly Ser Ala
            525             530             535 gtg gcc ctg agc gcc gcg agc tac acg tcc agc aac ccg cag tgg gac    1728
Val Ala Leu Ser Ala Ala Ser Tyr Thr Ser Ser Asn Pro Gln Trp Asp
540             545             550             555 gtg acc atc agc ttt gcg ccg ggc acc gtg atc gag tac aag tac atc    1776
Val Thr Ile Ser Phe Ala Pro Gly Thr Val Ile Glu Tyr Lys Tyr Ile
            560             565             570 aac gtg gcg agc agc ggg gcc gtg acc tgg gag gcc gac ccg aac cac    1824
Asn Val Ala Ser Ser Gly Ala Val Thr Trp Glu Ala Asp Pro Asn His
            575             580             585 acg tac acg gtc ccg gcg tcc tgc gcc acg gcc gcc gtc gtg tct gac    1872
Thr Tyr Thr Val Pro Ala Ser Cys Ala Thr Ala Ala Val Val Ser Asp
            590             595             600 acg tgg cag acg tga                                                1887
Thr Trp Gln Thr
605

<210> SEQ ID NO 6
<211> LENGTH: 628
<212> TYPE: PRT
<213> ORGANISM: Artificial Sequence
<220> FEATURE:
<223> OTHER INFORMATION: Synthetic Construct

<400> SEQUENCE: 6

Met Arg Leu Ser Thr Ser Ser Leu Phe Leu Ser Val Ser Leu Leu Gly
    -20             -15             -10

Lys Leu Ala Leu Gly Leu Thr Pro Ala Glu Trp Arg Ser Gln Ser Ile
-5              -1  1           5               10

Tyr Phe Leu Leu Thr Asp Arg Phe Gly Arg Thr Asp Asn Ser Thr Thr
            15              20              25

Ala Ala Cys Asp Thr Ser Asp Arg Val Tyr Cys Gly Gly Ser Trp Gln
            30              35              40

Gly Ile Ile Asn Gln Leu Asp Tyr Ile Gln Gly Met Gly Phe Thr Ala
        45              50              55

Ile Trp Ile Thr Pro Val Thr Gly Gln Phe Tyr Glu Asn Thr Gly Asp
60              65              70              75

Gly Thr Ser Tyr His Gly Tyr Trp Gln Gln Asp Ile Tyr Asp Leu Asn
            80              85              90

Tyr Asn Tyr Gly Thr Ala Gln Asp Leu Lys Asn Leu Ala Asn Ala Leu
            95              100             105

His Glu Arg Gly Met Tyr Leu Met Val Asp Val Val Ala Asn His Met
        110             115             120

Gly Tyr Asp Gly Ala Gly Asn Thr Val Asp Tyr Ser Val Phe Asn Pro
    125             130             135

Phe Ser Ser Ser Tyr Phe His Pro Tyr Cys Leu Ile Ser Asn Tyr
140             145             150             155

Asp Asn Gln Thr Asn Val Glu Asp Cys Trp Leu Gly Asp Thr Thr Val
            160             165             170
```

```
Ser Leu Pro Asp Leu Asp Thr Thr Ser Thr Ala Val Arg Asn Ile Trp
            175                 180                 185
Tyr Asp Trp Val Ala Asp Leu Val Ala Asn Tyr Ser Ile Asp Gly Leu
        190                 195                 200
Arg Val Asp Thr Val Lys His Val Glu Lys Asp Phe Trp Pro Gly Tyr
        205                 210                 215
Asn Ser Ala Ala Gly Val Tyr Cys Val Gly Glu Val Tyr Ser Gly Asp
220                 225                 230                 235
Pro Ala Tyr Thr Cys Pro Tyr Gln Asn Tyr Met Asp Gly Val Leu Asn
            240                 245                 250
Tyr Pro Ile Tyr Tyr Gln Leu Leu Tyr Ala Phe Glu Ser Ser Ser Gly
            255                 260                 265
Ser Ile Ser Asp Leu Tyr Asn Met Ile Ser Ser Val Ala Ser Ser Cys
        270                 275                 280
Lys Asp Pro Thr Leu Leu Gly Asn Phe Ile Glu Asn His Asp Asn Pro
        285                 290                 295
Arg Phe Ala Ser Tyr Thr Ser Asp Tyr Ser Gln Ala Lys Asn Val Ile
300                 305                 310                 315
Thr Phe Ile Phe Leu Ser Asp Gly Ile Pro Ile Val Tyr Ala Gly Gln
            320                 325                 330
Glu Gln His Tyr Ser Gly Gly Ser Asp Pro Ala Asn Arg Glu Ala Thr
            335                 340                 345
Trp Leu Ser Gly Tyr Ser Thr Ser Ala Thr Leu Tyr Thr Trp Ile Ala
        350                 355                 360
Thr Thr Asn Gln Ile Arg Ser Leu Ala Ile Ser Lys Asp Ala Gly Tyr
        365                 370                 375
Val Gln Ala Lys Asn Asn Pro Phe Tyr Ser Asp Ser Asn Thr Ile Ala
380                 385                 390                 395
Met Arg Lys Gly Thr Thr Ala Gly Ala Gln Val Ile Thr Val Leu Ser
            400                 405                 410
Asn Lys Gly Ala Ser Gly Ser Ser Tyr Thr Leu Ser Leu Ser Gly Thr
            415                 420                 425
Gly Tyr Ser Ala Gly Val Thr Leu Val Glu Thr Tyr Thr Cys Thr Thr
            430                 435                 440
Val Thr Val Asp Ser Ser Gly Asn Leu Pro Val Pro Met Thr Ser Gly
        445                 450                 455
Leu Pro Arg Val Phe Val Pro Ser Ser Trp Val Asn Gly Ser Ala Leu
460                 465                 470                 475
Cys Asn Thr Thr Gly Thr Gly Gly Ser Thr Gly Thr Thr Thr Ala Ser
            480                 485                 490
Glu Thr Gly Gly Ser Ser Pro Thr Ser Thr Ala Cys Ala Ser Val Pro
            495                 500                 505
Val Thr Phe Asn Glu Lys Val Thr Thr Val Val Gly Glu Thr Ile Lys
        510                 515                 520
Ile Ser Gly Ser Val Ala Ala Leu Gly Asp Trp Ala Thr Gly Ser Ala
        525                 530                 535
Val Ala Leu Ser Ala Ala Ser Tyr Thr Ser Ser Asn Pro Gln Trp Asp
540                 545                 550                 555
Val Thr Ile Ser Phe Ala Pro Gly Thr Val Ile Glu Tyr Lys Tyr Ile
            560                 565                 570
Asn Val Ala Ser Ser Gly Ala Val Thr Trp Glu Ala Asp Pro Asn His
            575                 580                 585
```

-continued

```
Thr Tyr Thr Val Pro Ala Ser Cys Ala Thr Ala Ala Val Val Ser Asp
        590                 595                 600
Thr Trp Gln Thr
    605
```

ALPHA-AMYLASES AND POLYNUCLEOTIDES ENCODING SAME

CROSS-REFERENCE TO RELATED APPLICATIONS

This application is a division of U.S. application Ser. No. 14/653,154 filed Jun. 17, 2015, now U.S. Pat. No. 9,765,317, which is a 35 U.S.C. 371 national application of PCT/US2013/074957 filed Dec. 13, 2013 which claims priority or the benefit under 35 U.S.C. 119 of U.S. provisional application No. 61/738,145 filed Dec. 17, 2012 the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to alpha-amylases, polynucleotides encoding the alpha-amylases, methods of producing the alpha-amylases, and methods of using the alpha-amylases. In embodiments of the present disclosure, raw starch degrading activity is improved.

Description of the Related Art

Enzymatic degradation of starch is part of many industrial processes including brewing, production of glucose or high fructose syrups and production of drinking or fuel ethanol. In its natural state, starch is quite resistant against degradation by many enzymes, and therefore industrial enzymatic degradation of starch is traditionally initiated by a heating step where starch is gelatinized, which renders the starch more sensitive to many enzymes. Some enzymes are able to act on ungelatinized starch, and are commonly referred to as having raw starch degrading activity. The use of these enzymes permits for improved processes, including, for example, reducing the heating step in processing starch.

Alpha-amylases (alpha-1,4-glucan 4 glucanohydrolases, EC. 3.2.1.1) constitute a group of enzymes which catalyze hydrolysis of starch and other linear and branched 1,4 glucosidic oligo and polysaccharides. Alpha-amylase enzymes have been used for a variety of different industrial purposes, including starch liquefaction, ethanol production, textile desizing, textile washing, starch modification in the paper and pulp industry, brewing, and baking.

WO 2010/091221 discloses a polypeptide having alpha-amylase activity from *Aspergillus terreus*. Database UniProt XP002576027 discloses the nucleic acid sequence from the Q0C881 (*Aspergillus terreus*) genome for an alpha-amylase.

WO 2008/080093 discloses alpha-amylases and glucoamylases and their use in making biofuel.

There remains a need in the art for improved alpha-amylases, including alpha-amylases that have raw starch degrading activity.

SUMMARY OF THE INVENTION

The present invention relates to polypeptides having alpha amylase activity selected from the group consisting of:

(a) a polypeptide comprising or consisting of an amino acid sequence of the mature polypeptide of the amino acid sequence of SEQ ID NO: 2, SEQ ID NO:4 or SEQ ID NO:6;

(b) a polypeptide comprising an amino acid sequence having at least 80% sequence identity to the mature polypeptide of the amino acid sequence of SEQ ID NO: 2, SEQ ID NO:4 or SEQ ID NO:6;

(c) a polypeptide encoded by a polynucleotide that hybridizes under medium stringency conditions with the mature polypeptide coding sequence of SEQ ID NO: 1, SEQ ID NO:3 or SEQ ID NO:5. In embodiments, polypeptides of the present disclosure are isolated.

The present invention also relates to polynucleotides encoding the polypeptides of the present invention; nucleic acid constructs; recombinant expression vectors; recombinant host cells comprising the polynucleotides; and methods of producing the polypeptides.

The present invention further relates to a transgenic plant, plant part or plant cell transformed with a polynucleotide encoding a polypeptide of the present invention.

In yet further aspects, the present invention relates to compositions comprising a polypeptide of the present invention, including compositions for producing ethanol.

The present invention also relates to method for the production of ethanol using a polypeptide of the present invention. The present invention also relates to method for the production of ethanol from ungelatinized starch using a polypeptide of the present invention.

Definitions

Alpha-amylase activity: The term "alpha-amylase activity" is defined herein as an activity that catalyzes the endohydrolysis of (1,4)-alpha-D-glucosidic linkages in polysaccharides containing three or more (1,4)-alpha-linked D-glucose units. The term "alpha-amylase activity" corresponds to the enzymes grouped in E.C. 3.2.1.1. For purposes of the present invention, alpha-amylase activity is determined according to the procedure described in the "Example" section.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide of the present invention having one or more (e.g., several) amino acids absent from the amino and/or carboxyl terminus of a mature polypeptide or domain, wherein the fragment has alpha-amylase activity. In one aspect, a fragment contains at least 497 amino acid residues, at least 526 amino acid residues, or at least 555 amino acid residues of SEQ ID NOS: 2 or 6. In another aspect, a fragment contains at least 528 amino acid residues, at least 559 amino acid residues, or at least 590 amino acid residues of SEQ ID NO:4.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample. For example, the polypeptide of the present invention may be used in industrial applications in the form of a fermentation broth product, that is, the polypeptide of the present invention is a component of a fermentation broth used as a product in industrial applications (e.g., ethanol production). The fermentation broth product will in addition to the polypeptide of the present invention comprise additional ingredients used in the fermentation process, such as, for example, cells (including, the host cells containing the gene encoding the polypeptide of the present invention which are used to produce the polypeptide of interest), cell debris, biomass, fermentation media and/or fermentation products. The fermentation broth may optionally be subject to one or more purification (including filtration) steps to remove or reduce one more components of a fermentation process. Accordingly, an "isolated" polypeptide of the present invention may be present in such a fermentation broth product.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino) as compared to another host cell expressing the same polynucleotide.

In one aspect, the mature polypeptide is amino acids 1 to 585 of SEQ ID NO: 2 based on the SignalP (Nielsen et al., 1997, Protein Engineering 10: 1-6) that predicts amino acids −1 to −21 of SEQ ID NO: 2 are a signal peptide.

In another aspect, the mature polypeptide is amino acids 1 to 622 of SEQ ID NO: 4 based on the SignalP (Nielsen et al., 1997, Protein Engineering 10: 1-6) that predicts amino acids −1 to −21 of SEQ ID NO: 4 are a signal peptide.

In another aspect, the mature polypeptide is amino acids 1 to 607 of SEQ ID NO: 6 based on the SignalP (Nielsen et al., 1997, Protein Engineering 10: 1-6) that predicts amino acids −1 to −21 of SEQ ID NO: 6 are a signal peptide.

Mature polypeptide coding sequence: The term "mature polypeptide coding sequence" means a polynucleotide that encodes a mature polypeptide having alpha-amylase activity.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having alpha-amylase activity.

Variant: The term "variant" means a polypeptide having alpha-amylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

DETAILED DESCRIPTION OF THE INVENTION

Polypeptides Having Alpha-Amylase Activity

In embodiments, the present disclosure relates to new alpha-amylase sequences. The new alpha-amylase sequences include the mature polypeptide of SEQ ID NO: 2, the mature polypeptide of SEQ ID NO:4 and the mature polypeptide of SEQ ID NO:6. A mature polypeptide of SEQ ID NO:2 is also shown as the amino acid sequence of SEQ ID NO: 1 (residues 1-585). A mature polypeptide of SEQ ID NO:4 is also shown as the amino acid sequence of SEQ ID NO: 3 (residues 1-622). A mature polypeptide of SEQ ID NO:6 is shown as the amino acid sequence of SEQ ID NO: 5 (residues 1-607).

In an embodiment, the present invention relates to isolated polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In one aspect, the polypeptides differ from the mature polypeptide of SEQ ID NO: 2 by no more than 10 amino acids, e.g., 1, 2, 3, 4, 5, 6, 7, 8, or 9 amino acids.

In another aspect, the polypeptide comprises or consists of the mature polypeptide of SEQ ID NO: 2. A polypeptide of the present invention preferably comprises or consists of the amino acid sequence of SEQ ID NO: 2 or an allelic variant thereof; or is a fragment thereof having alpha-amylase activity.

In an embodiment, the present invention relates to isolated polypeptides having a sequence identity to the mature polypeptide of SEQ ID NO:4 of at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In one aspect, the polypeptides differ from the mature polypeptide of SEQ ID NO:4 by no more than 10 amino acids, e.g., 1, 2, 3, 4, 5, 6, 7, 8, or 9 amino acids.

In another aspect, the polypeptide comprises or consists of the mature polypeptide of SEQ ID NO: 4. A polypeptide of the present invention preferably comprises or consists of the amino acid sequence of SEQ ID NO: 4 or an allelic variant thereof; or is a fragment thereof having alpha-amylase activity.

In an embodiment, the present invention relates to isolated polypeptides having a sequence identity to the polypeptide of SEQ ID NO:6 of at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In one aspect, the polypeptides differ from the mature polypeptide of SEQ ID NO:6 by no more than 10 amino acids, e.g., 1, 2, 3, 4, 5, 6, 7, 8, or 9 amino acids.

In another aspect, the polypeptide comprises or consists of the mature polypeptide of SEQ ID NO: 6. A polypeptide of the present invention preferably comprises or consists of the amino acid sequence of SEQ ID NO: 6 or an allelic variant thereof; or is a fragment thereof having alpha-amylase activity.

The present invention relates to an isolated polypeptide having alpha-amylase activity encoded by a polynucleotide that hybridizes medium stringency conditions, medium-high stringency conditions, high stringency conditions, or very high stringency conditions with a nucleic acid sequence encoding the mature polypeptide coding sequence of SEQ ID NO: 1, SEQ ID NO:3, or SEQ ID NO:5, or (ii) the full-length complement of the mature polypeptide coding sequence of SEQ ID NO: 1, SEQ ID NO:3, or SEQ ID NO:5.

In another embodiment, the present invention relates to an isolated polypeptide having alpha-amylase activity encoded by a polynucleotide having a sequence identity to the mature polypeptide coding sequence of SEQ ID NO: 1, SEQ ID NO:3 or SEQ ID NO:5 of at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, SEQ ID NO:4, or SEQ ID NO:6 comprising a substitution, deletion, and/or insertion at one or more (e.g., several) positions. In an embodiment, the number of amino acid substitutions, deletions and/or insertions introduced into the mature polypeptide is not more than 10, e.g., 1, 2, 3, 4, 5, 6, 7, 8 or 9 amino acids.

The amino acid changes may be of a minor nature, that is conservative amino acid substitutions or insertions that do not significantly affect the folding and/or activity of the protein. Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Variants of the polypeptides may be constructed on the basis of the polynucleotide presented as the mature polypeptide coding sequence, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Polynucleotides

The present invention also relates to isolated polynucleotides encoding a polypeptide of the present invention, as described herein. In one aspect, the present invention relates to polynucleotides that hybridizes under medium stringency conditions, medium-high stringency conditions, high stringency conditions, or very high stringency conditions with (i) the mature polypeptide coding sequence of SEQ ID NO: 1, SEQ ID NO: 3 or SEQ ID NO: 5, or (ii) the full-length complement of the mature polypeptide coding sequence of SEQ ID NO: 1, SEQ ID NO: 3 or SEQ ID NO: 5.

In another embodiment, the present invention relates to an a polynucleotide having a sequence identity to the mature polypeptide coding sequence of SEQ ID NO: 1, SEQ ID NO: 3 or SEQ ID NO: 5, of at least 80%, at least 85%, at least 90%, at least 91%, at least 92%, at least 93%, at least 94%, at least 95%, at least 96%, at least 97%, at least 98%, or at least 99%.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E.* coli lac operon, E. coli trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

Examples of origins of replication for use in a yeast host cell are the 2 micron origin of replication, ARS1, ARS4, the combination of ARS1 and CEN3, and the combination of ARS4 and CEN6.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The host cell may be any cell useful in the recombinant production of a polypeptide of the present invention, e.g., a prokaryote (bacterial cell) or a eukaryote (such as a mammalian, insect, plant, or fungal cell).

In a preferred aspect, the host cell is a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: a) cultivating a host cell comprising the polynucleotide encoding the polypeptide of the present invention operably linked to one or more control sequences that direct the production of the polypeptide under conditions conducive for production of the polypeptide; and (b) recovering the polypeptide.

In a preferred aspect, the cell is an *Aspergillus* cell, such as, *Aspergillus foetidus, Aspergillus fumigatus, Aspergillus*

*japonicus, Aspergillus nidulans, Aspergillus niger, Aspergillus oryzae, Aspergillus terreus.*

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Compositions

The present invention also relates to compositions comprising a polypeptide of the present invention. Such polypeptide compositions may be prepared in accordance with methods known in the art and may be in the form of a liquid or a dry composition. The polypeptide to be included in the composition may be stabilized in accordance with methods known in the art.

The polypeptide composition may be in the form of granulate, a micro granulate or a powder. Methods of preparing such compositions are well known in the art.

The polypeptide composition may be in the form of a fermentation broth product. The fermentation broth product will in addition to the polypeptide of the present invention comprise additional ingredients used in the fermentation process, such as, for example, cells (including, the host cells containing the gene encoding the polypeptide of the present invention which are used to produce the polypeptide of interest), cell debris, biomass, fermentation media and/or fermentation products. The fermentation broth may optionally be subject to one or more purification (including filtration) steps to remove or reduce one more components of a fermentation process.

The polypeptide composition may further comprise an enzyme selected from the group comprising of another alpha-amylase (EC 3.2.1.1), a beta-amylase (E.C. 3.2.1.2), a glucoamylase (E.C. 3.2.1.3), a pullulanases (E.C. 3.2.1.41), a phytase (E.C. 3.1.2.28) and a protease (E.C. 3.4.), and combinations thereof (e.g., the polypeptide of the present invention and a glucoamylase. or the polypeptide of the present invention and a glucoamylase and a protease).

In a particular aspect, the polypeptide composition further comprises a glucoamylase. The polypeptide may be combined with commercial glucoamylase, such as, the glucoamylase preparation supplied by Novozymes A/S as SPIRIZYME FUEL. The glucoamylase may also be derived from a strain of *Aspergillus* sp., such as *Aspergillus niger*, or from a strain of *Talaromyces* sp. and in particular derived from *Talaromyces leycettanus* such as the glucoamylase disclosed in U.S. Pat. No. Re. 32,153, *Talaromyces duponti* and/or *Talaromyces thermopiles* such as the glucoamylases disclosed in U.S. Pat. No. 4,587,215 and more preferably derived from *Talaromyces emersonii*. In one aspect, the glucoamylase is derived from *Talaromyces emersonii* strain CBS 793.97 and/or having the sequence disclosed as SEQ ID NO: 7 in WO 99/28448. In another aspect, the glucoamylase activity is derived from a strain of the genus *Trametes*, preferably *Trametes cingulata*. Further glucoamylases include the glucoamylase having the amino acid sequence of the mature polypeptide of SEQ ID NO: 2 in WO 2006/069289. Glucoamylase may also include glucoamylases from the genus *Pachykytospora*, preferably *Pachykytospora papyracea* or the *E. coli* strain deposited at DSMZ and given the no. DSM 17105, and including the glucoamylase having the amino acid sequence of the mature polypeptide of mature polypeptide of SEQ ID NO: 5 in WO 2006/069289. Further glucoamylases include those which have an amino acid sequence having at least 50%, at least 60%, at least 70%, at least 80%, at least 90%, at least 95%, at least 96%, at least 97%, at least 98%, or even at least 99% homology to the aforementioned amino acid sequence.

The dosage of the polypeptide composition of the invention and other conditions under which the composition is used may be determined on the basis of methods known in the art.

Uses

The present invention is also directed to methods for using the polypeptides having alpha-amylase activity, or compositions thereof.

The polypeptide or the composition of the present invention may be used in starch conversion, starch to sugar conversion and ethanol production etc, e.g., in liquefying and/or saccharifying a gelatinized starch, a granular starch, or a partly gelatinized starch. A partly gelatinized starch is a starch which to some extent is gelatinized, i.e., wherein part of the starch has irreversibly swelled and gelatinized and part of the starch is still present in a granular state.

The polypeptide or the composition of the present invention may be used in a process for liquefying a gelatinized starch, a granular starch, or a partly gelatinized starch substrate in aqueous medium with the polypeptide of the present invention.

A preferred use of a polypeptide of the present invention is in a fermentation process to produce glucose and/or maltose suitable for conversion into a fermentation product by a fermenting organism, preferably a yeast. Such fermentation processes include a process for producing ethanol for fuel or drinking ethanol (portable alcohol), a process for producing a beverage, a process for producing desired organic compounds, such as citric acid, itaconic acid, lactic acid, gluconic acid, sodium gluconate, calcium gluconate, potassium gluconate, glucono delta lactone, or sodium erythorbate; ketones; amino acids, such as glutamic acid (sodium monoglutaminate), but also more complex compounds such as antibiotics, such as penicillin, tetracyclin; enzymes; vitamins, such as riboflavin, B12, beta-carotene; hormones, which are difficult to produce synthetically.

In a preferred embodiment, the polypeptide of the present invention is used in a process comprising fermentation to produce a fermentation product (e.g., ethanol), from a gelatinized starch. Such a process for producing ethanol from gelatinized starch by fermentation comprises: (i) liquefying the gelatinized starch with a polypeptide with alpha-amylase activity of the present invention; (ii) saccharifying the liquefied mash obtained; (iii) fermenting the material obtained in step (ii) in the presence of a fermenting organism. Optionally the process further comprises recovery of the ethanol. The saccharification and fermentation may be carried out as a simultaneous saccharification and fermentation process (SSF process).

In another preferred embodiment, the polypeptide of the present invention is used in a process comprising fermentation to produce a fermentation product, e.g., ethanol, from an ungelatinized ("raw") starch. Such a process for producing ethanol from ungelatinized starch-containing material by fermentation comprises: (i) contacting the ungelatinized starch with a polypeptide with alpha-amylase activity of the present invention to degrade the ungelatinized starch; (ii) saccharifying the mash obtained; (iii) fermenting the material obtained in step (ii) in the presence of a fermenting organism. Optionally the process further comprises recovery of the ethanol. The saccharification and fermentation may be carried out as a simultaneous saccharification and fermentation process (SSF process).

The starch-containing material used in the methods of the present invention may be any starch-containing plant material. Preferred starch-containing materials are selected from the group consisting of: tubers, roots and whole grains; and any combinations thereof. In an embodiment, the starch-containing material is obtained from cereals. The starch-containing material may, e.g., be selected from the groups consisting of corn (maize), cob, wheat, barley, cassava, sorghum, rye, milo and potato; or any combination thereof. When the fermentation product is ethanol the starch-containing material is preferably whole grains or at least mainly whole grains. The raw material may also consist of or comprise a side-stream from starch processing.

In further embodiments, the polypeptide of the present invention may also be useful in textile, fabric or garment desizing by treating a textile fabric or garment with a polypeptide of the prense invention, in producing a baked good or dough, by treating a dough with a polypeptide of the present invention, and optionally baking, as an ingredient in a detergent and pulp and paper production process by treating a paper making pulp with a polypeptide of the present invention.

The present invention is further described by the following examples that should not be construed as limiting the scope of the invention.

EXAMPLES

Assays for Alpha-Amylase Activity

1. Phadebas Assay

Alpha-amylase activity is determined by a method employing Phadebas® tablets as substrate. Phadebas tablets (Phadebas® Amylase Test, supplied by Pharmacia Diagnostic) contain a cross-linked insoluble blue-colored starch polymer, which has been mixed with bovine serum albumin and a buffer substance and tableted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given alpha-amylase will hydrolyze a certain amount of substrate and a blue color will be produced. The color intensity is measured at 620 nm. The measured absorbance is directly proportional to the specific activity (activity/mg of pure alpha-amylase protein) of the alpha-amylase in question under the given set of conditions.

2. Alternative Method

Alpha-amylase activity is determined by a method employing the PNP-$G_7$ substrate. PNP-$G_7$, which is an abbreviation for p-nitrophenyl-alpha,D-maltoheptaoside, is a blocked oligosaccharide which can be cleaved by an endo-amylase. Following the cleavage, the alpha-Glucosidase included in a commercially available kit digests the substrate to liberate a free PNP molecule which has a yellow color and thus can be measured by visible spectophometry at λ=405 nm (400-420 nm). Kits containing PNP-$G_7$ substrate and alpha-Glucosidase are commercially available from Roche and others.

To prepare the reagent solution 10 ml of substrate/buffer solution is added to 50 ml enzyme/buffer solution as recommended by the manufacturer. The assay is performed by transferring 20 micro l sample to a 96 well microtitre plate and incubating at 25° C. 200 micro l reagent solution pre-equilibrated to 25° C. is added. The solution is mixed and pre-incubated 1 minute and absorption is measured every 30 sec. over 4 minutes at OD 405 nm in an ELISA reader.

The slope of the time dependent absorption-curve is directly proportional to the activity of the alpha-amylase in question under the given set of conditions.

Example 1

An alpha-amylase of the present invention (SEQ ID NO:2) was evaluated in a raw starch fermentation assay and compared to both a hybrid alpha-amylase (described in WO 2006/069290 as having the *Rhizomucor pusillus* catalytic domain (SEQ ID NO:20), the *Aspergillus niger* linker (SEQ ID NO: 72) and the *Aspergillus niger* carbohydrate binding domain (SEQ ID NO:96)) and to the *Aspergillus terreus* alpha-amylase (shown as SEQ ID NO:2 in WO 2010/091221).

Materials and Methods

Approximately 405 g yellow dent corn (obtained from Hawkeye Renewables of Shell Rock, Iowa; ground in-house) was added to 595 g tap water and the dry solids (DS) level was determined to be 34.42% DS. This mixture was supplemented with 3 ppm penicillin and 1000 ppm urea. The slurry was adjusted to pH 4.5 with 40% $H_2SO_4$. Approximately 5 g of this slurry was added to 15 mL tubes. Each tube was dosed with purified DK193 AMG (*Trametes cingulata* AMG disclosed in WO 2006/069289 as SEQ ID NO: 2) at 0.0801 mg EP/g DS and the alpha-amylases were dosed at 0.0225 mg EP/g DS. Actual enzyme dosages were based on the exact weight of corn slurry in each tube according to the following formula:

$$Enz. \text{ dose } (\mu L) = \frac{\text{Final } enz. \text{ dose (mg/g } Ds) \times \text{Mash weight (g)} \times \text{Dry solid content (\% } DS)}{\text{Stock enzyme conc. (mg/mL)} \times 1000}$$

Water was added to each tube to bring the total added volume (enzyme+water) to 2% of the initial weight of the mash. This volume correction brings all tubes in the experiment to the same total percent solids, making ethanol concentrations directly comparable between treatments. After enzyme and water addition, 200 μL of yeast propagate (0.024 g Fermentis Ethanol Red yeast, incubated overnight at 32° C. in 50 mL filtered liquefied corn mash and 5.1 μL Spirizyme Plus AMG) was added to each tube.

Tubes were incubated in a temperature controlled room at 32° C. and six replicate fermentations of each treatment were run. All tubes were vortexed at 24 and 48 hours. One sample was sacrificed for HPLC analysis at 24 hours, two at 48 hours, and three at 70 hours. The HPLC preparation consisted of stopping the reaction by addition of 50 μL of 40% $H_2SO_4$, centrifuging for 10 min at 1462×g, and filtering through a 0.45 μm filter. Samples were stored at 4° C. An Agilent™ 1100 HPLC system coupled with RI detector was used to determine ethanol and oligosaccharides concentrations. The separation column was a BioRad™ Aminex HPX-87H ion exclusion column (300 mm×7.8 mm).

Data were analyzed in JMP (SAS, Cary, N.C.). Outliers were removed based on F-test (p<0.05). Treatments were compared to control with the Tukey-Kramer HSD test (p<0.05).

Results and Discussion

As shown in Table 1, under these experimental conditions, an alpha-amylase of the present invention (SEQ ID NO: 2) performed better than the hybrid alpha-amylase (WO 2006/069290) showing a 2.2% improvement at the 70 hr time point as compared to the hybrid alpha-amylase (WO 2006/069290) and also better than the *Aspergillus terreus* alpha-amylase.

TABLE 1

| Treatment (70 hr) | Ethanol yield |
| --- | --- |
| Invention (SEQ ID NO: 2) | 102.21% |
| Hybrid alpha-amylase of WO 2006/069290 | 100.00% |
| *A. terreus* | 96.68% |

Example 2

Materials and Methods

Approximately 405 g yellow dent corn (obtained from Hawkeye Renewables of Shell Rock, Iowa; ground in-house) was added to 595 g tap water and the dry solids (DS) level was determined to be 34.42% DS. This mixture was supplemented with 3 ppm penicillin and 1000 ppm urea. The slurry was adjusted to pH 4.5 with 40% $H_2SO_4$. Approximately 5 g of this slurry was added to 15 mL tubes. Each tube was dosed with purified DK193 AMG at 0.0623 mg EP/g DS and the alpha-amylases were dosed at 0.0175 mg EP/g DS. Actual enzyme dosages were based on the exact weight of corn slurry in each tube according to the following formula:

$$\text{Enz. dose (μL)} = \frac{\text{Final enz. dose (mg/g } Ds) \times \text{Mash weight (g)} \times \text{Dry solid content(\% } DS)}{\text{Stock enzyme conc. (mg/mL)} \times 1000}$$

Water was added to each tube to bring the total added volume (enzyme+water) to 2% of the initial weight of the mash. This volume correction brings all tubes in the experiment to the same total percent solids, making ethanol concentrations directly comparable between treatments. After enzyme and water addition, 200 μL of yeast propagate (0.024 g Fermentis Ethanol Red yeast, incubated overnight at 32° C. in 50 mL filtered liquefied corn mash and 5.1 μL Spirizyme Plus AMG) was added to each tube.

Tubes were incubated in a temperature controlled room at 32° C. and six replicate fermentations of each treatment were run. All tubes were vortexed at 24 and 48 hours. One sample was sacrificed for HPLC analysis at 24 hours, two at 48 hours, and three at 70 hours. The HPLC preparation consisted of stopping the reaction by addition of 50 μL of 40% H2SO4, centrifuging for 10 min at 1462xg, and filtering through a 0.45 μm filter. Samples were stored at 4° C. An Agilent™ 1100 HPLC system coupled with RI detector was used to determine ethanol and oligosaccharides concentrations. The separation column was a BioRad™ Aminex HPX-87H ion exclusion column (300 mm×7.8 mm).

Data were analyzed in JMP (SAS, Cary, N.C.). Outliers were removed based on F-test (p<0.05). Treatments were compared to control with the Tukey-Kramer HSD test (p<0.05).

Results and Discussion

As shown in Table 2, under these experimental conditions, an alpha-amylase of the present invention (SEQ ID NO: 2) performed better than the *Aspergillus terreus* alpha-amylase showing a 1.5% improvement at the 70 hr time point. The other alpha-amylases (SEQ ID NO:4 and SEQ ID NO:6) also performed better the *Aspergillus terreus* alpha-amylase.

TABLE 2

| Treatment (70 hr) | Ethanol yield |
| --- | --- |
| Invention (SEQ ID NO: 2) | 101.5% |
| Invention (SEQ ID NO: 4) | 101.1% |
| Invention (SEQ ID NO: 6) | 100.3% |
| *A. terreus* | 100.0% |

The invention claimed is:

1. A recombinant host cell comprising a polynucleotide encoding a polypeptide having alpha-amylase activity, wherein the polynucleotide is operably linked to one or more control sequences that direct the production of the polypeptide, and wherein the polypeptide is selected from the group consisting of:
   (a) a polypeptide comprising the amino acid sequence of the mature polypeptide of the amino acid sequence of SEQ ID NO: 2, SEQ ID NO:4, or SEQ ID NO:6;
   (b) a polypeptide comprising the amino acid sequence having at least 90% sequence identity to the mature polypeptide of the amino acid sequence of SEQ ID NO: 2, SEQ ID NO:4, or SEQ ID NO:6; and
   (c) a polypeptide encoded by a polynucleotide having at least 90% sequence identity to the mature polypeptide coding sequence of SEQ ID NO: 1, SEQ ID NO:3, or SEQ ID NO:5.

2. A method of producing a polypeptide having alpha-amylase activity, comprising:
   (a) cultivating a host cell under conditions conducive for production of the polypeptide, wherein the host cell comprises a polynucleotide encoding a polypeptide having alpha-amylase activity, wherein the polynucleotide is operably linked to one or more control sequences that direct the production of the polypeptide, and wherein the polypeptide is selected from the group consisting of:
      (i) a polypeptide comprising the amino acid sequence of the mature polypeptide of the amino acid sequence of SEQ ID NO: 2, SEQ ID NO:4, or SEQ ID NO:6;
      (ii) a polypeptide comprising the amino acid sequence having at least 90% sequence identity to the mature polypeptide of the amino acid sequence of SEQ ID NO: 2, SEQ ID NO:4, or SEQ ID NO:6; and
      (iii) a polypeptide encoded by a polynucleotide having at least 90% sequence identity to the mature polypeptide coding sequence of SEQ ID NO: 1, SEQ ID NO:3, or SEQ ID NO:5; and
   (b) recovering the polypeptide.

3. The host cell of claim 1, wherein the polypeptide comprises an amino acid sequence having at least 95% sequence identity to the mature polypeptide of the amino acid sequence of SEQ ID NO: 2, SEQ ID NO:4, or SEQ ID NO:6.

4. The host cell of claim 1, wherein the polypeptide is encoded by a polynucleotide having at least 95% sequence identity to the mature polypeptide coding sequence of SEQ ID NO:1, SEQ ID NO:3, or SEQ ID NO:5.

5. The host cell of claim 1, wherein the polypeptide comprises an amino acid sequence having least at 97% sequence identity to the mature polypeptide of the amino acid sequence of SEQ ID NO: 2, SEQ ID NO:4, or SEQ ID NO:6.

6. The host cell of claim 1, wherein the polypeptide is encoded by a polynucleotide having at least 97% sequence identity to the mature polypeptide coding sequence of SEQ ID NO:1, SEQ ID NO:3, or SEQ ID NO:5.

7. The host cell of claim 1, wherein the polypeptide comprises or consists of residues 1-585 of SEQ ID NO: 2 or the mature polypeptide encoded by SEQ ID NO: 1.

8. The host cell of claim 1, wherein the polypeptide comprises or consists of residues 1-622 of SEQ ID NO: 4 or the mature polypeptide encoded by SEQ ID NO: 3.

9. The host cell of claim 1, wherein the polypeptide comprises or consists of residues 1-607 of SEQ ID NO: 6 or the mature polypeptide encoded by SEQ ID NO: 5.

10. The host cell of claim 1, wherein the host cell is a yeast cell.

11. The host cell of claim 10, wherein the yeast host cell is a *Candida*, *Hansenula*, *Kluyveromyces*, *Pichia*, *Saccharomyces*, *Schizosaccharomyces*, or *Yarrowia* cell.

12. The host cell according to claim 10, wherein the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cell.

13. The host cell according to claim 10, wherein the yeast host cell is a *Saccharomyces cerevisiae* cell.

14. The method of claim 2, wherein the polypeptide comprises an amino acid sequence having at least 95% sequence identity to the mature polypeptide of the amino acid sequence of SEQ ID NO: 2, SEQ ID NO:4, or SEQ ID NO:6.

15. The method of claim 2, wherein the polypeptide is encoded by a polynucleotide having at least 95% sequence identity to the mature polypeptide coding sequence of SEQ ID NO:1, SEQ ID NO:3, or SEQ ID NO:5.

16. The method of claim 2, wherein the polypeptide comprises an amino acid sequence having at least 97% sequence identity to the mature polypeptide of the amino acid sequence of SEQ ID NO: 2, SEQ ID NO:4, or SEQ ID NO:6.

17. The method of claim 2, wherein the polypeptide is encoded by a polynucleotide having at least 97% sequence identity to the mature polypeptide coding sequence of SEQ ID NO:1, SEQ ID NO:3, or SEQ ID NO:5.

18. The method of claim 2, wherein the polypeptide comprises or consists of residues 1-585 of SEQ ID NO: 2 or the mature polypeptide encoded by SEQ ID NO: 1.

19. The method of claim 2, wherein the polypeptide comprises or consists of residues 1-622 of SEQ ID NO: 4 or the mature polypeptide encoded by SEQ ID NO: 3.

20. The method of claim 2, wherein the polypeptide comprises or consists of residues 1-607 of SEQ ID NO: 6 or the mature polypeptide encoded by SEQ ID NO: 5.

* * * * *